United States Patent
Baumgart (10) Patent No.: US 7,826,884 B2
(45) Date of Patent: Nov. 2, 2010

(54) LIVE FLUOROSCOPIC ROADMAPPING INCLUDING TARGETED AUTOMATIC PIXEL SHIFT FOR MISREGISTRATION CORRECTION

(75) Inventor: John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 927 days.

(21) Appl. No.: 11/554,082

(22) Filed: Oct. 30, 2006

(65) Prior Publication Data

US 2008/0027316 A1    Jan. 31, 2008

Related U.S. Application Data

(60) Provisional application No. 60/834,446, filed on Jul. 31, 2006.

(51) Int. Cl.
   *A61B 5/05*   (2006.01)
   *A61B 6/00*   (2006.01)
   *G06K 9/00*   (2006.01)
   *G01N 23/04* (2006.01)

(52) U.S. Cl. .................. 600/407; 600/431; 600/425; 382/130; 382/132; 378/62

(58) Field of Classification Search ............. 600/407, 600/436, 431, 425; 382/128, 276, 176, 282, 382/294, 130, 131, 283, 278, 295, 132; 378/65, 378/62

See application file for complete search history.

(56) References Cited

U.S. PATENT DOCUMENTS

| | | | |
|---|---|---|---|
| 4,870,692 A * | 9/1989 | Zuiderveld et al. ........... 382/107 |
| 4,995,064 A | 2/1991 | Wilson et al. | |
| 5,077,769 A | 12/1991 | Franciose | |
| 5,369,678 A | 11/1994 | Chiu et al. | |
| 5,690,106 A | 11/1997 | Bani-Hashemi et al. | |
| 5,956,435 A * | 9/1999 | Buzug et al. ................ 382/283 |
| 6,083,168 A * | 7/2000 | Hossack et al. ............. 600/443 |
| 6,370,417 B1 * | 4/2002 | Horbaschek et al. ........ 600/424 |

(Continued)

OTHER PUBLICATIONS

Meijering et al., "Image Registration for Digital Subtraction Angiography", International Journal of Computer Vision, 31(2/3), 1999, pp. 227-246.*

*Primary Examiner*—Eric F Winakur
*Assistant Examiner*—Katherine L Fernandez (57) ABSTRACT

An X-ray diagnostic imaging system for conducting live fluoroscopic subtraction imaging is described as including an X-ray source for directing X-ray radiation to a patient being examined, an x-ray imaging device positioned for receiving the X-ray radiation and acquiring images in response thereto and a processor arranged in communication with the x-ray source and x-ray imaging device to control acquisition of a contrast-enhanced mask image frame and a live image frame without contrast enhancement, to conduct a pixel shift calculation operation based on a small, user-defined region of interest (ROI), for example, 1/16 of a full frame, to realize a pixel shift vector to correct for motion between live image frames, to shift pixels comprising the mask image frame by pixel shift directions defined by the pixel shift vector, and to subtract the shifted mask image frame from the live image frame to realize a live roadmapping image frame. The system includes a display for displaying the live roadmapping image frame, and a user interface that allows a user to define and capture the small ROI in the displayed image frame for use by the processor conducting the pixel shift calculation.

23 Claims, 4 Drawing Sheets

U.S. PATENT DOCUMENTS 7,406,187 B2 * 7/2008 Sato et al. .................. 382/128
7,545,967 B1 * 6/2009 Prince et al. ................ 382/130
2005/0089143 A1 * 4/2005 Nakano et al. ........... 378/98.12

* cited by examiner

LIVE FLUOROSCOPIC ROADMAPPING INCLUDING TARGETED AUTOMATIC PIXEL SHIFT FOR MISREGISTRATION CORRECTION

PRIORITY CLAIM TO RELATED APPLICATION

This application claims priority from U.S. Provisional Patent Application Ser. No. 60/834,446, filed Jul. 31, 2006, the disclosure of which is incorporated by reference in its entirety herein.

BACKGROUND OF THE INVENTION

The present invention relates to subtraction angiography, and more particularly relates to an X-ray diagnostic imaging system and method for dynamically targeting and instantaneously correcting for motion between acquired frames in angiographic roadmapping procedures.

Angiography refers generally to the capture and representation of blood vessels or vasculature of the human body by means of X-ray imaging, i.e., X-ray vascular imaging. X-ray diagnostic imaging systems may be used for angiographic imaging procedures such as digital subtraction angiography (DSA), and live fluoroscopic roadmapping. Digital subtraction angiography or DSA is an imaging method used for visualizing blood vessels inside a patient's body that includes injecting a contrast medium bolus that is substantially opaque to X-rays into the blood vessels or vasculature under study as images are acquired by the X-ray diagnostic imaging system. Prior to acquisition of the contrast image, a mask image without contrast is acquired. A difference image is calculated by superimposing upon and subtracting the mask image from the contrast image. Ideally, nothing appears in the difference image other than the image of the blood vessels. Because of the time difference between acquisition of the mask image (no contrast) and acquisition of the contrast-enhanced images, global and periodic motion, fluctuations in the intensity of the X-ray source, scattering by the contrast medium, etc., unwanted artifacts may appear in the differenced or digitally subtracted angiographic image. U.S. Pat. No. 5,690,106, to Bani-Hashemi, et al. ("the '106 patent"), discloses a flexible image registration system for conducting digital subtraction angiography (DSA) with a C-arm rotational X-ray system.

Like DSA, fluoroscopic roadmapping is an angiographic imaging method for vascular imaging in which two images are overlayed to visualize blood vessels in a particular bodily area, e.g., the chest area. But unlike DSA, roadmapping includes superimposing upon and subtracting a stored 2D contrast-enhanced image (i.e., a mask image) from a current or live fluoroscopic image of the same vessel area (i.e., a non-contrast-enhanced image). Because only the stored mask image is acquired while the vessels are opacified with contrast medium the patient is generally exposed to lower levels of contrast agent as compared with a DSA study. Typically, live fluoroscopic or fluoro imaging uses lower radiation intensity as compared to DSA. U.S. Pat. No. 4,995,064 (the '064 patent"), commonly-owned, discloses an X-ray examination apparatus that may be used for live fluoroscopic ("fluoro") roadmapping.

Live fluoro roadmapping supports various endovascular procedures such as percutaneous transluminal coronary angioplasty, where the contrast image is superimposed on a series of live 2D fluoro images acquired while a catheter is moved through the vasculature under study. The acquired mask or contrast image frame is superimposed on the real-time non-contrast-enhanced live frames as they are acquired, and subtracted in real time. The result is a static display of the vascular structures, typically displayed in white, while the catheter appears in black. Like DSA, however, misregistration due to global and periodic motion, etc., can result in image artifacts in the subtracted live fluoro roadmapping, which degrade image quality.

To correct for misregistration, various conventional processes have developed. For example, U.S. Pat. No. 4,870,692 discloses a method of correcting subtraction images for patient motion in a fluoroscopy system. The method includes automatically dissecting the mask and contrast images into subregions. The pixels in those subregions are then compared using a cross-correlation correction algorithm. The cross-correlation correction algorithm ideally calculates a shift vector based on a portion of the image that has shifted by motion in one or more sub-images. The shift vector shifts the mask image to better align it with the non-contrast enhanced image or images of the same position. For each shift vector, there are several storage locations for storing its position, direction components and reliability criteria for each component.

Another known method, somewhat related to the current inventive x-ray imaging system and method for live fluoro roadmapping includes automatic sampling the acquired live images or frames (non contrast-enhanced) into the system's background process, which searches a large arbitrary region of interest (ROI) for the "best" shift vector. The sampling and searching, however, is very operation intensive and not conducive to accurate real-time correction. This is because the automatic sample, search and compare process must search the entire large region to generate the best shift vector using conventional methods. In particular, the large area for search and comparison is typically a center quarter (¼) of the image frame, or one quarter (¼) of the image area that contains the greatest amount of image or feature information.

Accordingly, there is an inherent latency in updating or generating and applying an accurate shift vector to correct for, and minimize artifacts in the live roadmapping images. Such latency is typically on the order of 1 to 2 seconds. While the conventional method may correct for gradual accumulated movement, such as the table being moved, or drifting of the source and/or detection device, it may be ineffective for periodic motion artifacts. Periodic motion artifacts can be generated by patient head or chest movement during breathing, or heart beating, or by oscillation of the table or C-arm if bumped. Nor will such a conventional shift vector-based method correct for motion in a targeted area that has a different motion artifact than another area that has not been searched and compared, for example, generated by motion that is coplanar with the X-ray detector.

SUMMARY OF THE INVENTION

The present invention provides a system and method that overcomes the shortcomings of prior art methods that correct for misregistration between frames acquired in live fluoro roadmapping. The inventive method receives user or clinician direction to dynamically calculate a pixel shift vector based on a much smaller region of interest (ROI) of an image than used in the methods of the known art. More particularly, the clinician viewing the live 2D images (no contrast) during the live fluoro roadmapping is able to use an input device such as a trackball or joystick to select a small ROI in any part of the live fluoro image. The system and method then automatically compares the pixels comprising the small ROI with the pixels comprising a counterpart small ROI in the mask frame, and calculates a next best shift vector thereby. Correction for any misalignment is made based on the next best shift vector based on the pixel subset searched and compared. Preferably, the small ROI is on the order of 1/16 of the entire image frame to maintain required to conduct the function and implement it in the live fluoro roadmapping image displayed timely.

The search and comparison may be implemented with a discrete sign change algorithm, of any known pixel search and compare function that can be efficiently implemented. The result of the subtraction is scored or rated for quality of registration. Based on the scoring, the test shift amount may be changed, and the inventive process is repeated over the entire search space. The scoring represents the best registration and therefore the best shift vector for use with the subtractions, based on the user-chosen small ROI. For that matter, the inventive process may carry out an additional calculation to determine fractional pixels to be shifted as well as whole pixels.

In one embodiment, the invention includes a method for live fluoroscopic roadmapping with an X-ray diagnostic imaging system, which allows users to control the focus of the dynamic correction. The system continuously corrects for motion between acquired frames during the live roadmapping. The method includes acquiring a contrast-enhanced mask image frame of a patient under examination, acquiring a live image frame that is not contrast-enhanced in the same imaging position of the mask frame acquisition, responding to user input which defines a small region of interest (ROI) upon which the dynamic pixel-shift function will be automatically carried out, analyzing the small ROI in the live frame with a corresponding small ROI in the mask image frame to calculate a shift vector for shifting the mask image frame before subtraction from the live image frame, shifting the mask image frame using the shift vector, and subtracting the shifted mask frame from the live image frame to generate the live roadmapping frame. The function is implemented seamlessly, in the background process, as the user continues modifying at will the position of the small ROI in the current live roadmapping frames for use in analyzing to calculate a next best shift vector.

DESCRIPTION OF DRAWING FIGURES

An understanding of embodiments of the present invention can be gained from the following detailed description of the invention, taken in conjunction with the accompanying drawings of which.

DETAILED DESCRIPTION OF EXEMPLARY EMBODIMENTS OF THE INVENTION

The inventive methods, software and apparatus set forth herein are disclosed and described in order to convey the broad inventive concepts. The drawings and descriptions are not meant to in any way limit the scope and spirit of the inventions, as claimed.

Reference will now be made in detail to exemplary embodiments of the present invention, examples of which are illustrated in the accompanying drawings, wherein like reference numerals refer to like elements throughout. The terms "process" and "method" are generally used to refer to a series of operations performed by a processor, be it a central processing unit of an x-ray system for live fluoro roadmapping, or a secondary processing unit of such a system. Useful machines for performing exemplary operations of the present invention include the AXIOM family of X-ray diagnostic imaging systems and products, by Siemens Medical Systems. The inventive method or process, however, is not limited to implementation on Siemens' X-ray diagnostic imaging systems, but may be implemented in any known or future X-ray system arranged for conducting real-time X-ray subtraction imaging, including live fluoroscopic procedures.

Figure 1:
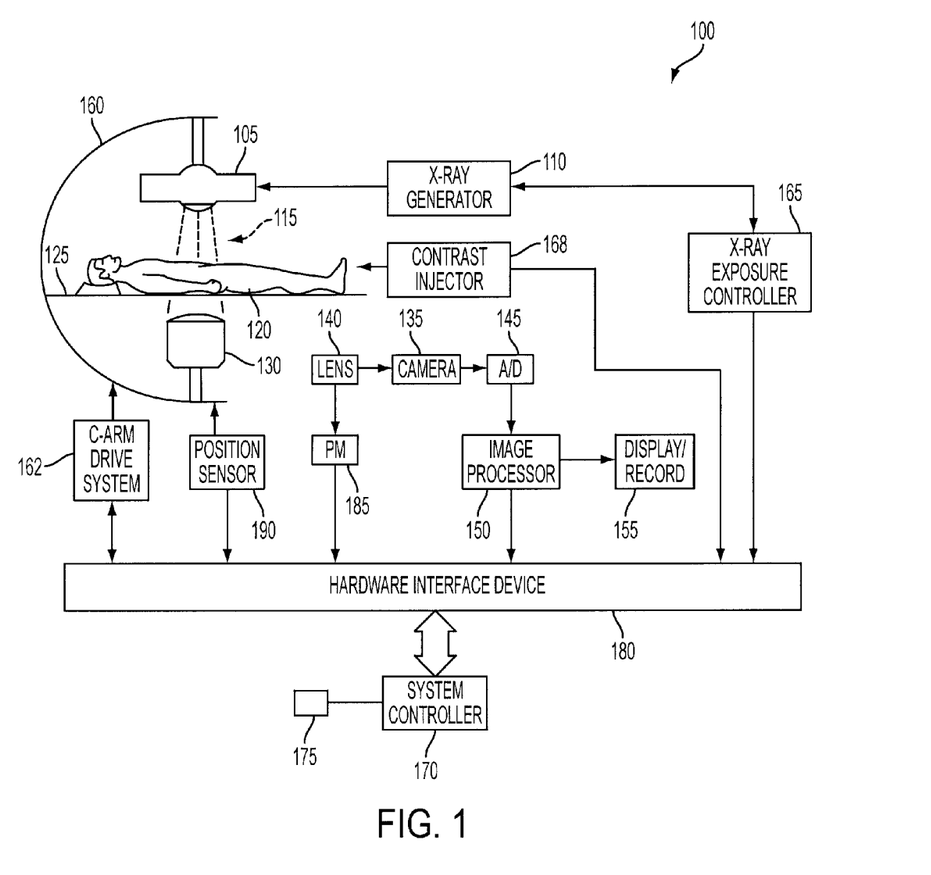
FIG. 1 schematic diagram depicting an X-ray diagnostic imaging system constructed to operate with an image intensifier to carry out live fluoro roadmapping with targeted automatic pixel shift of the invention.

FIG. 1 depicts an X-ray diagnostic imaging system 100 for live fluoro roadmapping that includes the dynamic targeted automatic pixel shift ability of the invention. X-ray system 100 includes an x-ray tube or source 105 supplied by an X-ray power generator 110 for generating an X-ray beam 115. A patient 120 is shown supported on a patient-support table 125 so that the generated X-ray beam 115 passes through him/her onto an X-ray image intensifier tube 130 located on the patient support table 125 opposite the X-ray source. The image intensifier tube 130 provides an optical output that is imaged into a camera 135 such as a television camera, or video display camera and the like by means of a lens system 140. Although the image intensifier tube would normally be arranged along an axis parallel to the axis of the X-ray beam input, a perpendicular path for the optical output is illustrated in FIG. 1 for viewing convenience and clarity. A video signal supplied from the camera 135 is digitized in an analog to digital (A/D) converter 145, and processed in an image processor 150. A display/record device 155 records and/displays the processed image(s), e.g., subtracted angio images, preferably in DICOM format. The reader should note that display/record device 155 includes a display for displaying the displayed image output, and a separate device for archiving. The image is arranged for storage in such a archive, e.g., a network device, in a DICOM format. The only exception is a VCR or DVR record, which stores a recorded version of the live displayed image, without transforming the image frame(s) into DICOM device; DVR and VCR are not DICOM devices.

A C-arm gantry arrangement 160 is provided to move the X-ray source 105 and image intensifier tube 130 in a controlled manner with respect to patient support table 125, by a C-arm drive system 162. An X-ray exposure controller 165, contrast medium injector 168 and system controller 170 are also included. System controller 170 may be a personal computer or any known controller capable of receiving and transmitting control signals to/from the above-described X-ray system components via a hardware interface 180. System controller 170 includes a user input device 175, such as a trackball, mouse, joystick, and/or computer keyboard to provide for user input in carrying out various system functions, such as the dynamic targeting and automatic pixel shift function during live roadmapping, and other system operation such as mode selection, linearity control, X-ray dose control, data storage, etc. Lens system 140 may include a beam splitting arrangement to direct a portion of the light responsive to an acquired X-ray image to a photomultiplier tube 185 to generate a light level responsive signal. The light level responsive signal is used by X-ray exposure controller 165 for controlling X-ray exposure. A position measuring device or sensor 190 is included to accurately indicate the relative position between the C-arm 160 and patient support table 125.

An embodiment of the invention is implemented by X-ray diagnostic imaging system 100 as follows. A clinician or other user view the real-time 2D subtraction images during a live fluoro roadmapping procedure may position a small ROI (for example, 1/16 of the image area or less) within a broader area of interest using the user input device 175, connected to system controller 170. The position of the small ROI is displayed as a box, circle or some kind of marking on the live image being display in real time while the ROI is moved about the image with the input device. A shift vector is calculated by the system controller 170, image processor 150 or other processor based on the small ROI, and used in the imaging pipeline after a displayable image has been computed. The shift vector is then available for application in for the subtraction process when the following x-ray frame is ready for processing. Because of the reduced size of the ROI chosen, the search and compare function generates and applies each updated shift vector so there is no detectable latency.

That is, the small ROI is sized so that the shift vector calculations using such a sub-frame can be conducted for every frame, up to and exceeding 30 frames per second. Each test subtraction requires all of the pixels in the ROI to be subtracted and scored, wherein the time needed is proportional to the number of small ROI-included pixels, or pixel portions, chosen by user input. The search space and searching time is dependent upon the number of possibilities in the ROI for best shift amounts, correlating to the number of searches to be performed by the process. The amount is fixed based on the image size. The binary search for the best vector is proportional to the base 2 log of the size of the search space, or fixed image size.

Figure 2:
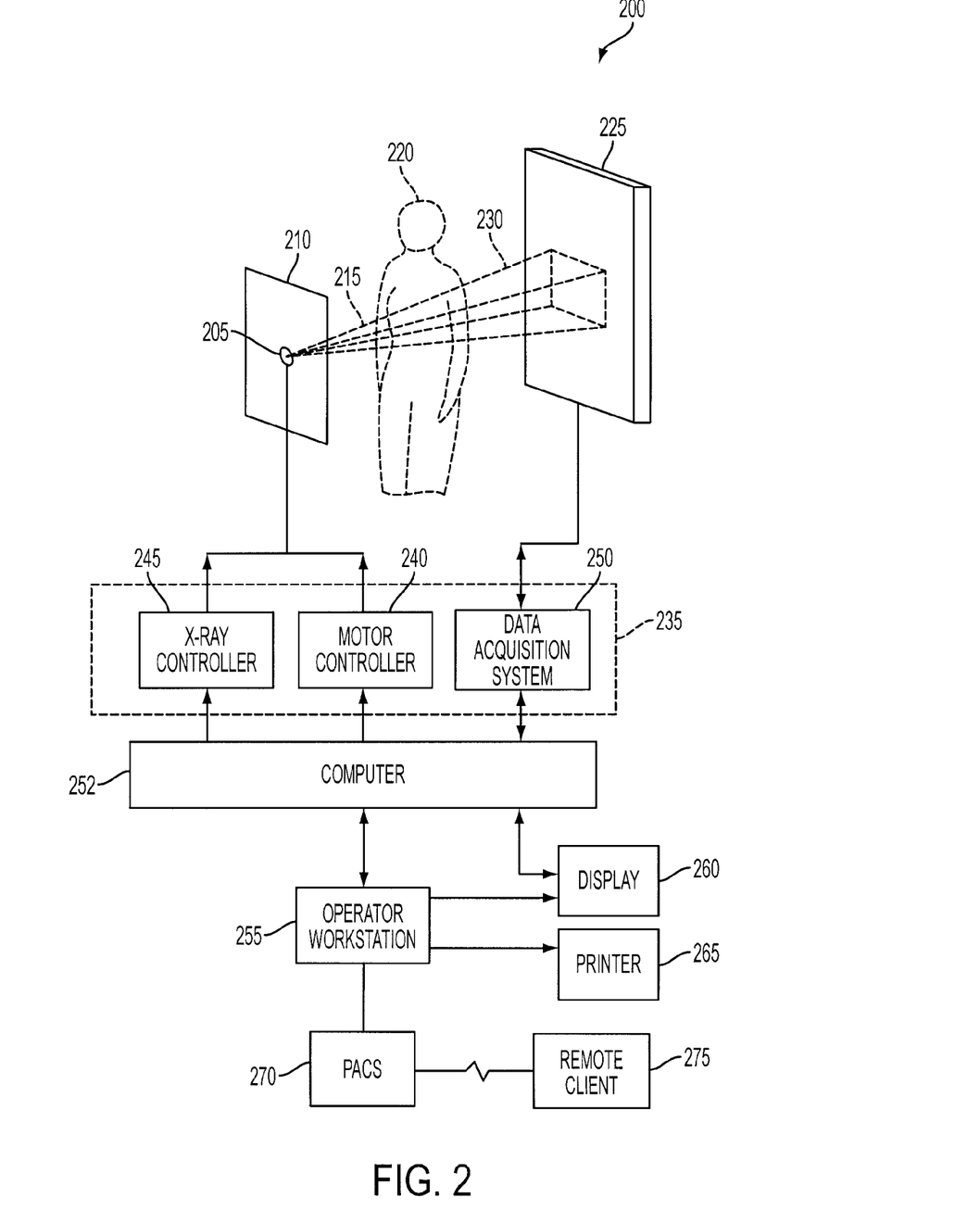
FIG. 2 is schematic diagram depicting an X-ray diagnostic imaging system constructed to operate with a flat panel detector to carry out live fluoro roadmapping with targeted automatic pixel shift of the invention.

FIG. 2 shows a second embodiment of an X-ray diagnostic imaging system 200 arranged for acquiring and processing fluoroscopic images, and for implementing an exemplary dynamic automatic pixel shift operation of the invention. System 200 includes an X-ray source 205, such as an X-ray tube and associated support and filtering components. The X-ray source may be affixed to a support, such as a C-arm fluoroscope stand, or examination table, which would allow the X-ray source to be moved within a constrained region. The constrained region may be arcuate or otherwise three dimensional, depending on the nature of the support structure. For simplicity, the constrained region of FIG. 2 is depicted as a plane 210, within which the source 205 may move in two dimensions. A collimator may also be included, which will define the size and shape of X-ray beam 215 emerging from the source.

The beam 215 passes through a patient 220 and impacts an X-ray detector 225. In practice, X-ray detector 225 may comprise an image intensifier, such as image intensifier 130 of system 100 depicted in FIG. 1 herein. For that matter, while the inventive X-ray system 100 is an image intensifier-based system for implementing the dynamic pixel shift vector calculation for fluoroscopic roadmapping, system 200 is a preferred system for implementing an embodiment of the invention. And as should be obvious to the skilled artisan, that x-ray diagnostic imaging system 200, because it does not require a traditional image intensifier, such as image intensifier 130 of FIG. 1, does not require certain parts of the FIG. 1 image intensifier imaging chain, i.e., photomultiplier tube (PM) 185, lens device 140, A/D converter 145 and camera 135. Instead, a flat panel detector such as detector 225 of FIG. 2 instead acquires digital image frames directly, which are then transferred to the image processor (processor 150 of FIG. 1).

For real-time viewing, the image may be acquired by system 200 using a video camera with a charge-coupled device (CCD), or comprise a flat detector array. In such case, pixels comprising the flat detector array produce electrical signals representing the intensity of the incident X-rays. An X-ray shield with an opening for a stream of radiation 230 may be included to shield the clinician from X-ray scatter. X-ray source 12 is controlled by a system controller 235, which typically controls power and control signals for live fluoroscopic roadmapping and like fluoro procedures. The system controller 235 may execute signal processing and filtration functions, including the dynamic pixel shift analysis, and shifting function, upon receipt of user input defining the small ROI discussed in detail above. The system controller 235 moves the source 205 via motor controller 240, and may move the patient 220 and detector 225, and X-ray activation and operation via X-ray controller 245. The system controller may also include an acquisition system 250 in communication with the detector 225, to convert the data to digital signals for processing on a computer 252 (if required). The processed image data are reconstructed into an image that will include various regions of interest (ROI) for diagnosis and evaluation, and the dynamic pixel shift function for motion correction of the invention.

The computer 252 may be configured to control features enabled by system controller 235, and receive commands and scanning parameters via an operator workstation 255, equipped with a keyboard, mouse, joystick or other input device for user control of the small image region or ROI searched while system 200 implements the dynamic pixel shift function, and other operations. The computer 252 provides the live fluoro frames to a display 260. The operator workstation may control the displayed images as described, providing the images to a printer 265, and a PACS 270, which may communicate the fluoro images to a remote network, or client 275. Client 275 may be a radiology department information system (RIS), hospital information system (HIS), internal or external network or just a remote standalone work station.

Figure 3:
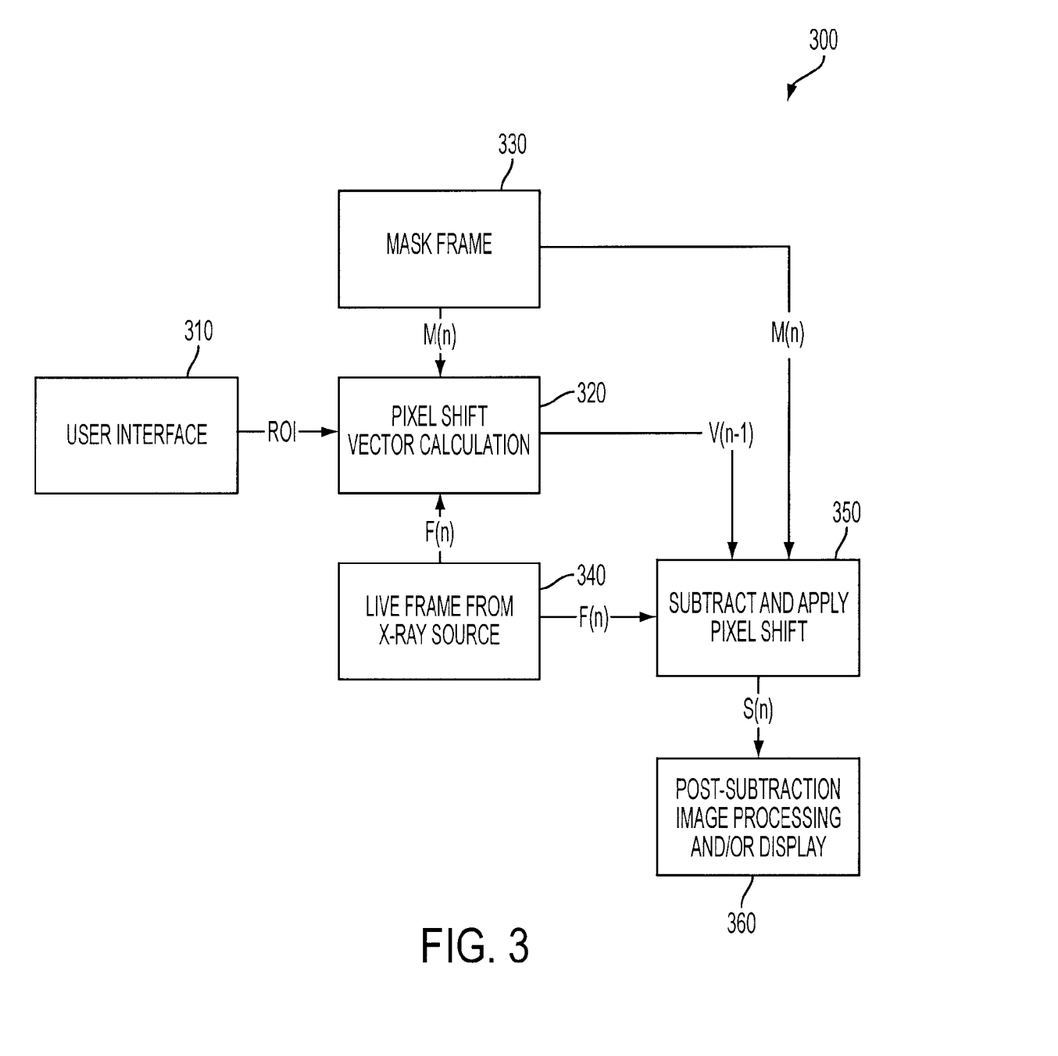
FIG. 3 is a schematic block diagram depicting the functional flow of the inventive targeted automatic shift vector calculation for real-time live fluoro roadmapping of the invention.

FIG. 3 depicts a schematic block diagram 300 that highlights an exemplary functional operation of the inventive live fluoro roadmapping process with dynamic pixel shift ability. The exemplary inventive functioning may be carried out in a system such as X-ray imaging system 100, and X-ray imaging system 200, or any other known X-ray fluoroscopy system that may be constructed to implement the FIG. 3 operation. Functional block 310 represents that the clinician chooses the small ROI (1/16 of a frame area) via a user interface, such as user device 175 or FIG. 1, or operator workstation 255 of FIG. 2. The small ROI or size of the sub-frame for the shift search and compare operation is the same wherever the user moves the cursor, or box within a live frame. The pixel coordinates are provided to a system controller, such as controller 170 of FIG. 1, or system controller 235 of FIG. 2. The system controller or other processor implements the search and compare operation based on the small ROI's user-defined position in the live frame.

Functional block 320 represents the search and compare for the shift vector calculation, and the calculation. That is, the small ROI-defined pixel coordinates are provided to a pixel shift calculator function in the background process to implement the search and compare and generate the shift vector. The dynamic process includes the input of a current mask frame (M(n)), indicated by functional block 320, and the input of a live frame (F(n)), indicated by functional block 340. Functional block 350 represents a portion of the process wherein a prior shift vector calculation (V (n−1)) is applied to the mask frame M (n) and so the live frame F (n) during the subtraction. A subtracted result (S (n)) may be displayed, or subjected to further processing. Such display is represented by functional block 360. A shift of (0, 0) may be applied to the mask for the first subtracted image displayed. The background process is carried out in a processor such as processor 150 of FIG. 1, or computer 250 of FIG. 2, coordinated with the system controller.

Figure 4:
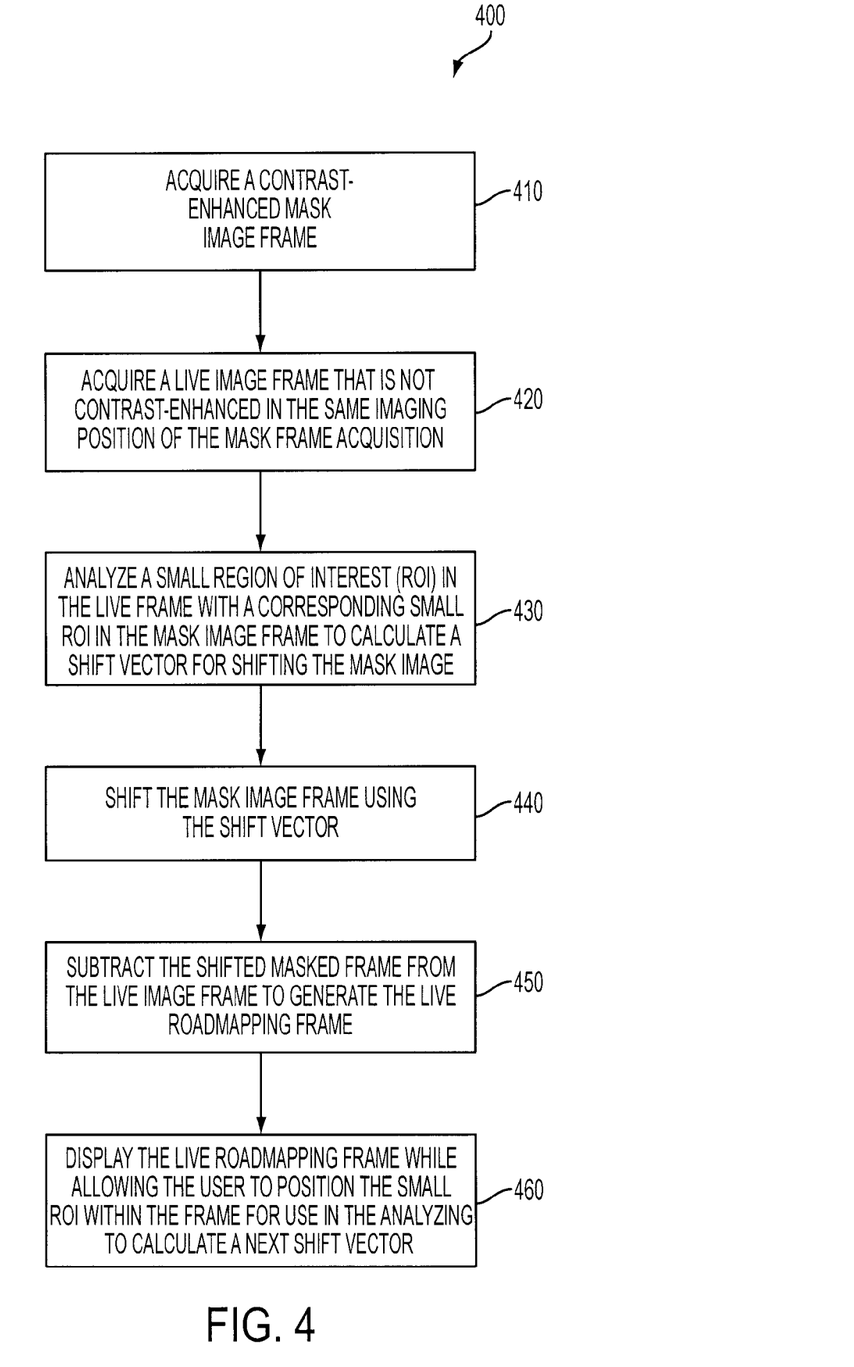
FIG. 4 is a schematic flow diagram of a method for carrying out the inventive targeted automatic shift vector calculation, and misregistration correction thereby for real-time live fluoro roadmapping of the invention.

FIG. 4 is a schematic flow diagram depicting an exemplary method 400 for live fluoroscopic roadmapping of the invention. The exemplary inventive method allows for user control to dynamically correct for motion between acquired frames during the live roadmapping. Block 410 represents a step of acquiring a contrast-enhanced mask image frame of a patient under examination. Block 420 represents a step of acquiring a live image frame that is not contrast-enhanced in the same imaging position of the mask frame acquisition. Block 430 represents a step of analyzing the pixels in a small region of interest (ROI) in the live frame (user-defined) with a corresponding small ROI in the mask image frame to calculate a shift vector before subtraction from the live image frame. Block 440 represents a step of shifting the mask image frame using the shift vector. Block 450 represents a step of subtracting the shifted mask frame from the live image frame to generate the live roadmapping frame. Block 460 represents a step of displaying the live roadmapping frame while allowing the user to position the small ROI within the frame for use in the analyzing to calculate a next shift vector.

While not identified in FIG. 4, the method preferably uses an ROI that is about 1/16 of the size of the live image frames. The method does permit this ROI to be adjusted in size to achieve optimum performance and results. For example, the user may enlarge the size of the ROI to a maximum limited only by computation ability that will perform the inventive operation in a "live" timeframe. That is, the size of the ROI and therefore the amount of image which must be searched and compared to determine the next best shift vector limits the speed of the entire subtraction and display operation. The method also includes injecting contrast agent into the vasculature of the patient under examination, and is well suited for tracking medical instruments introduced into a patient during an interventional procedure.

Although a few examples of the present invention have been shown and described, it would be appreciated by those skilled in the art that changes might be made in these embodiments without departing from the principles and spirit of the invention, the scope of which is defined in the claims and their equivalents.

The invention claimed is:

1. An X-ray diagnostic imaging system for conducting live fluoroscopic subtraction imaging, comprising:
   an X-ray source for directing X-ray radiation to a patient being examined;
   an X-ray imaging device positioned for receiving the X-ray radiation and acquiring images in response thereto;
   a processor configured to communicate with the X-ray source and X-ray imaging device to control acquisition of a contrast-enhanced mask image frame and a live image frame without contrast enhancement, to conduct a pixel shift vector calculation operation based on a small, user-defined region of interest (ROI) having a location selectable by a user within a displayed image frame during live X-ray imaging and comprising a plurality of adjacent pixels to realize a pixel shift vector derived from the plurality of pixels to correct for motion between an individual live image frame of successive live image frames and a mask image frame, to shift pixels comprising the mask image frame by pixel shift directions defined by the pixel shift vector, and to subtract the shifted mask image frame from the live image frame to realize a live roadmapping image frame;
   a display for displaying live roadmapping image frames; and
   a user interface that allows a user to define and capture the small ROI in the displayed image frame for use by the processor conducting the pixel shift calculation.

2. The X-ray diagnostic imaging system as set forth in claim 1, wherein the live roadmapping image is scored for registration quality and
   said processor calculates a plurality of pixel shift vectors for a corresponding respective plurality of successive live image frames and shifts a mask image frame by said plurality of pixel shift vectors to provide a plurality of different mask image frames corresponding to said plurality of successive live image frames and subtracts the plurality of different mask image frames from the corresponding plurality of successive live image frames.

3. The X-ray diagnostic imaging system as set forth in claim 2, wherein said processor,
   automatically generates a test pixel shift vector,
   dynamically modifies the test pixel shift vector in response to the user-defined small ROI, and
   performs the subtraction operation over the entire frame using the updated pixel shift vector.

4. The X-ray diagnostic imaging system as set forth in claim 1, wherein the processor is configured to subtract and score all pixels in the user-defined small ROI for registration quality determination.

5. The X-ray diagnostic imaging system as set forth in claim 1, wherein the processor is configured to determine a shift for fractional pixels in the user-captured ROI input when the pixel shift vector is calculated.

6. The X-ray diagnostic imaging system as set forth in claim 1, wherein the size of the small ROI may be modified by user input, and wherein the processor is configured to calculate the pixel shift vector in a time that is proportional to the small ROI dimensions.

7. The X-ray diagnostic imaging system as set forth in claim 1, wherein the processor is configured to modify a form of the live roadmapping image frames to be DICOM compliant.

8. The X-ray diagnostic imaging system as set forth in claim 1, further comprising an image contrast injector and contrast injector control mechanism controllable via the user interface.

9. The X-ray diagnostic imaging system as set forth in claim 1, wherein the pixel shift vector calculation includes searching and comparing a subset of pixels in the live frame and mask frame captured by the small ROI using a discrete sign change operation.

10. The X-ray diagnostic imaging system as set forth in claim 1, wherein the pixel shift vector is determined for a small user-defined region of interest (ROI) of a live image and is applied to substantially the whole mask image frame.

11. The X-ray diagnostic imaging system as set forth in claim 1, further comprising a patient-support table, and wherein the X-ray source is mounted above or below the table.

12. The X-ray diagnostic imaging system as set forth in claim 1, further comprising a user work station including a display and user input device in order that the user may view the live roadmapping image on the display, and control and capture the small ROI in said image using the input device.

13. The X-ray diagnostic imaging system as set forth in claim 1, further comprising means for communicating the live roadmapping image frames to a remote location for viewing and/or storage.

14. A method for live fluoroscopic roadmapping with an X-ray diagnostic imaging system, which allows user control to dynamically correct for motion between acquired frames during the live fluoro roadmapping, the method comprising the steps of:

acquiring a contrast-enhanced mask image frame of a patient under examination;

acquiring a live image frame that is not contrast-enhanced in the same imaging position of the mask frame acquisition;

analyzing a small region of interest (ROI), defined by user input and having a location selectable by a user within a displayed image frame during live X-ray imaging and comprising a plurality of adjacent pixels, within the live image frame with a corresponding small ROI in the mask image frame, and calculating a shift vector using the plurality of pixels for shifting the mask image frame before subtraction from the live image frame based on the small ROI;

shifting substantially the whole mask image frame using the shift vector, and subtracting the shifted mask frame from the live image frame to generate the live roadmapping frame; and displaying the live roadmapping frame and responding to user positioning of the small ROI within the frame for capturing and analyzing pixels comprising the small ROI to calculate a next shift vector.

15. The method for live fluoroscopic roadmapping as set forth in claim 14, wherein the size of the small ROI corresponds to the time for analyzing and calculating the next shift vector.

16. The method for live fluoroscopic roadmapping as set forth in claim 15, wherein in response to the user adjusting the size of small ROI defining an image frame area, the processor analyzes the adjusted small ROI to calculate the shift vector and including the steps of calculating a plurality of pixel shift vectors for a corresponding plurality of successive live image frames and shifts a mask image frame by said plurality of pixel shift vectors to provide a plurality of different mask image frames corresponding to said plurality of successive live image subtracting the plurality of different mask image frames from the corresponding plurality of successive live image frames.

17. The method for live fluoroscopic roadmapping as set forth in claim 14, wherein the small ROI is displayed as a box superimposed on the displayed live roadmapping image.

18. The method for live fluorographic roadmapping as set forth in claim 14, wherein the processor is configured to automatically generate a test shift vector that shifts each pixel in the mask image frame in a direction (0,0) for use as the shift vector for the first live roadmapping frame.

19. The method for live fluoroscopic roadmapping as set forth in claim 14, wherein the step of acquiring the contrast-enhanced mask image frame includes first introducing an X-ray contrast agent into the patient's vasculature.

20. The method for live fluoroscopic roadmapping as set forth in claim 14, wherein the live roadmapping is carried out to follow progress of a catheter inserted into the patient's vasculature.

21. The method for live fluoroscopic roadmapping as set forth in claim 14, wherein the step of displaying includes displaying at a remote location.

22. The method for live fluoroscopic roadmapping as set forth in claim 14, further including processing for storing the live roadmapping image in DICOM format.

23. A program storage device readable by machine, tangibly embodying a program of instructions executable by the machine to perform method steps for live fluoroscopic roadmapping with an X-ray diagnostic imaging system, where the method allows for user control to dynamically correct for motion between acquired frames during the live fluoro roadmapping, as set forth in claim 14.

* * * * *